United States Patent [19]

Levine

[11] 4,183,910

[45] Jan. 15, 1980

[54] METHOD FOR TESTING TO PREDICT AND/OR DIAGNOSE ALLERGY TO PENICILLINS, AND COMPOUNDS AND COMPOSITIONS FOR USE IN SUCH TESTS

[76] Inventor: Bernard B. Levine, 210 Riverside Dr., New York, N.Y. 10025

[21] Appl. No.: 898,044

[22] Filed: Apr. 20, 1978

[51] Int. Cl.$^2$ .................. C07D 277/06; C07D 417/12; A61K 37/02; A61K 31/425
[52] U.S. Cl. .................. 424/9; 260/112.5 R; 424/177; 424/270; 560/170; 548/201
[58] Field of Search .................. 260/306.7 C; 424/270, 424/9

[56] References Cited

U.S. PATENT DOCUMENTS

| | | | |
|---|---|---|---|
| 3,592,804 | 7/1971 | Quitt et al. | 260/306.7 |
| 3,804,820 | 4/1974 | Quitt et al. | 260/306.7 |
| 3,867,365 | 2/1975 | Stohmann et al. | 424/9 |
| 3,979,508 | 9/1976 | Stuhmann et al. | 424/9 |

OTHER PUBLICATIONS

Hamilton-Miller et al., Biochem. Journal 123, 183-190, (1971).
Locher et al., Chem. Abs. 72, 41106a, (1969).
Clarke et al., "Chemistry of Penicillin", 1949, pp. 554-556.
Levine, II et al., Chem. Abs. 86, 72508, (1976).
Levine, I New Eng. J. Med. 275, 1115, (1966), refers to *Beth Israel Hospital Seminars*, 1969.
Levine et al., Int. Arch. Allergy 35, 445, (1969).
Levine, Chapter 83 in Manual Clinical Immunology.
Adkinson, Jr., *Resident and Staff Physician*, 1977, p. 55.
Levine III, New Eng. J. Med. 286, 42-43, (1972).
Levine IV, "Drug Allergy", (1971).
Levine et al., J. Allergy 43, 231-244, (1969).
Levine et al., J. Clin. Investigation 47, 556, (1968).

*Primary Examiner*—Mark L. Berch
*Attorney, Agent, or Firm*—Sughrue, Rothwell, Mion, Zinn and Macpeak

[57] ABSTRACT

The invention relates to the testing of humans or other animals, for allergic reaction or hypersensitivity to penicillins. The tests can be used both to predict and to diagnose allergy. The invention comprises new penicilloyl-polylysine (PPL) preparations, new materials for use in minor determinant mixture (MDM) compositions and novel test methods employing such materials.

The new PPL preparations comprise homogeneous, high purity, maximally coupled, α-diastereoisomeric, penicilloyl conjugates of low molecular weight PPLs. The PPL materials of the invention have the molecular structure in accordance with the following generic formula:

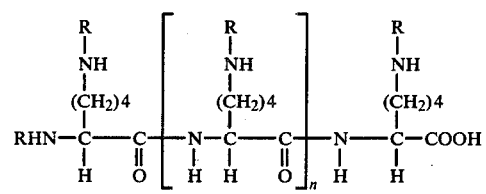

wherein:
R is selected from the group consisting of H and penicilloyl groups or similar groups derived from cephalosporins or other β-lactam antibiotics; and
n is an integer of from 4 to 10,
at least about 66% and up to 100% of the R groups are other than hydrogen. Solutions containing this PPL material are useful in skin testing for penicillin allergy or hypersensitivity alone, but preferably are utilized in a two-part test with MDM solutions containing the novel MDM materials of the invention.

The new MDM materials have the following structure:

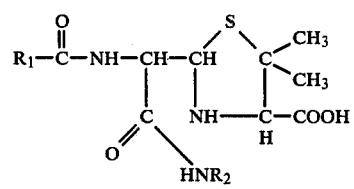

wherein:
$R_1$ = a side chain which defines the type of penicillin, the new material is a derivative of benzylpenicillin; and
$R_2$ is an alkyl group of $C_2$–$C_6$ length, or an aminoacid residue as described herein.

The tests are preferably carried out by applying solutions of the materials to the skin of the patient or other test animal and pricking or scratching the skin, or by injecting the materials intradermally, and then observing for wheal and flare reactions.

5 Claims, No Drawings

METHOD FOR TESTING TO PREDICT AND/OR DIAGNOSE ALLERGY TO PENICILLINS, AND COMPOUNDS AND COMPOSITIONS FOR USE IN SUCH TESTS

BACKGROUND OF THE INVENTION

1. Field Of The Invention

The invention provides novel PPL and MDM materials and compositions and more sensitive tests for predicting and diagnosing allergy or hypersensitivity to penicillin in humans or other animals by skin testing with the improved PPL and MDM compositions of the invention.

2. Discussion Of The Prior Art

Since the introduction of penicillins for therapeutic treatment of infections in humans and other animals, a variety of allergic reactions have been observed; the most serious of these reactions is anaphylactic shock, which is estimated to be the cause of several hundred deaths in the United States each year. The possibility of non-fatal anaphylaxis and urticarial reactions, which are much more common than fatal anaphylaxis, also is a matter of serious concern for the physician considering the treatment of a patient with penicillins.

Therefore, much research effort has been devoted to the development of reliable tests predictive of human allergic response or hypersensitivity to penicillin. As the result, certain skin tests have been described in the literature and are under study clinically. One such test generally involves scratching the skin in an area on which a test solution has been placed, or intradermally injecting the test solution, and observing for a positive reaction—i.e., a wheal-and-flare reaction around the scratch or injection sites formed within 15 minutes. More sensitive skin tests involve the intradermal injection of solutions containing (1) PPL and (2) MDM compositions.

The chemistry underlying the mechanism by which penicillin may trigger allergic reactions in humans and the details of the state of the art in "scratch" and "intradermal" skin tests is extensively set forth in the literature. The following are intended only as representative citations which provide useful technical background in the field of this invention:

"Immunological Mechanisms of Penicillin Allergy" B. B. Levine; J. New England Medicine, 275:1115 (1966)

"The Nature of the Antigen-Antibody Complexes Initiating the Specific Wheal-and-Flare Reaction in Sensitized Man" B. B. Levine, A. P. Redmond; J. Clinical Investigation, 47:556 (1968)

"Predictions of Penicillin Allergy by Immunological Tests" B. B. Levine, D. M. Zolov; J. of Allergy, 43:4:231 (1969)

"Drug Allergy" B. B. Levine; Reprint of Edited Remarks presented at seminar co-sponsored by John Hopkins U., Am. Acad. of Allergy and NIH (1971)

"Skin Rashes With Penicillin Therapy: Current Management" B. B. Levine; New England Journal of Medicine (1971)

"A Guide to Skin Testing for Penicillin Allergy" N. F. Adkinson, Jr., Resident and Staff Physician at Johns Hopkins U. (1977)

See also U.S. Pat. Nos. 3,867,365 and 3,979,508 issued to Stahmann and Wagle.

U.S. Pat. No. 3,867,365, noted above, describes one prior art PPL material used in penicillin allergy skin tests, and it is believed that such compounds may have been commercialized. The patented compositions over which my compositions are an improvement comprise BPO conjugates of a heterogeneous mixture of random polylysine polymers said to have from about 12 to 102 or more lysine units linked in the polymer chain.

In prior studies, such as those cited above, it has also been shown that some patients who are given penicillin therapeutically develop IgE antibodies to certain haptens which are formed from the reaction of the penicillin with tissue proteins. These include the benzylpenicilloyl (BPO) hapten, whose structure is well known, and certain "minor determinant" haptens whose structures are not yet known.

IgE antibodies are kown to mediate anaphylactic and other immediate allergic reactions to penicillin in man. These reactions are frequently severe, causing diffuse rash, difficulty in breathing, abdominal cramps and fainting, hypotension and arrythmia. They are capable of causing death due to cardiovascular collapse, ventricular arrythmia and/or respiratory obstruction.

Skin tests with various materials derived from penicillin have been shown to be positive in the presence of these IgE antibodies, and thus serve as a predictive test for severe penicillin allergy. The skin test compositions currently in use include benzylpenicilloyl-polylysine (BPL), which detects IgE antibodies specific for the BPO haptenic group, and the MDM, which detects IgE antibodies specific for the minor determinants.

Up to now, the MDM generally used has included combinations of two or more of benzylpencillin (PG), benzylpenicilloic acid (NaBPO), benzylpenilloic acid (POIC) and benzylpenicilloyl-amine (BPO-amine). The structures of the MDM materials used to date are set forth below:

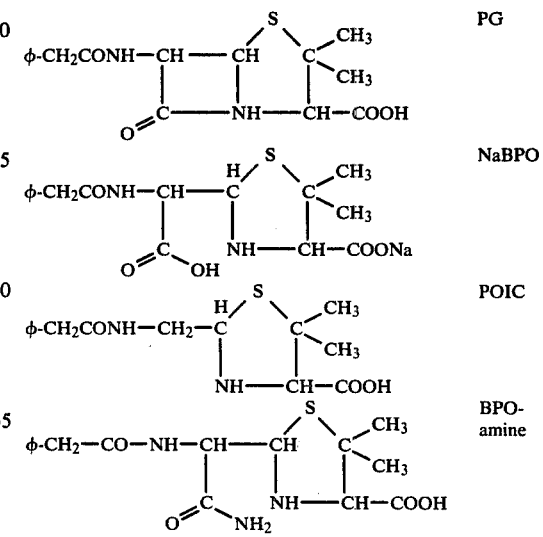

While intradermal testing using PPL and the MDM has proved very useful in predicting penicillin allergy, I have observed that with certain patients IgE antibodies induced by penicillin are undetected or only weakly detected by the MDM test compositions currently in use.

In accordance with my invention, I have observed that the addition of an N-penicilloyl-amine of an aliphatic amine or α-aminoacid, especially BPO-propyl amine or BPO-ethyl amine, to the MDM, greatly increases the intensity of the test.

With respect to my new PPL materials, I have observed a number of significant improvements over the prior art. First, my PPL materials are homogeneous, high purity materials which offer higher reproducibility from lot to lot than is provided by heterogeneous polylysine conjugates of the prior art. The new PPL materials of this invention also are substantially free from low molecular weight impurities (polylysine$_2$ and/or polylysine$_3$) and, therefore, minimize the chance of diffusion of compound from the test site into the bloodstream with the attendant possibility of constitutional reactions. Additionally, my relatively low molecular weight, $B_{4-13}$-$L_{6-12}$, materials would have a lower degree of immunogenicity than the higher molecular weight PPL conjugates of the prior art, and, thus, are less likely to induce allergy in a test subject. Further my PPL materials are of a molecular weight which allows sufficient diffusion in the skin from an intradermal or prick test site to give an intense wheal-and-flare reaction. By contrast, high molecular weight conjugates may diffuse less well in about one-fourth to one-third of patients and, thus, may not give a recognizably positive skin test in some allergic patients (Levine and Fellner, Journal of Allergy, 36:342–52 (1965).

In view of the possibly catastrophic consequences of observing a negative response in a patient who is actually allergic to penicillin, it is critical that the most sensitive and highly reliable allergy tests be made clinically available.

Further, the use of the most sensitive test is of importance when doing prick or scratch tests. These are much more convenient but less sensitive than intradermal tests. Thus, more sensitive test materials permit the use of a prick test.

Accordingly, the principal objective of my invention is to provide a more sensitive and reproducible skin test for penicillin allergy using improved PPL preparations and an improved MDM. Another purpose is to provide novel PPL and MDM compounds and compositions for use in skin testing for prediction or diagnosis of penicillin allergic reaction or hypersensitivity.

SUMMARY OF THE INVENTION

My invention comprises:

(1) New PPL preparations. The penicilloyl groups are the α-diastereoisomers. The polylysine carriers are linear homogeneous polymers having a degree of polymerization of from 6 to 12. The polylysine polymers may be prepared from L-, D-, or D,-L-lysines. These polymers are maximally coupled with penicilloyl groups. For example, in one material, the poly-L-lysine$_8$ carrier was over 97% pure, the balance being polylysine$_{6-7}$. This material was maximally coupled with 8 penicilloyl moieties. In other preparations of this PPL, from 6 to 9 penicilloyl moieties may be coupled to the polylysine$_8$ polymer chain.

(2) New MDM materials. The materials are N-penicilloyl-amines of an aliphatic amine or an α-aminoacid and MDM mixtures containing such materials. The N-penicilloyl amines or aminoacids may be α-diastereoisomers, other diastereoisomers or diastereoisomeric mixtures.

(3) Methods for skin testing for penicillin allergy or hypersensitivity using solutions containing the novel materials of (1) and (2) independently or in a two-solution, combined test. The new MDM materials may be used alone or as part of a multicomponent MDM. The skin tests may be prick, scratch or intradermal. Some of the compositions may also be useful for in vitro testing for penicillin allergy.

DETAILED DESCRIPTION OF THE INVENTION

My invention will be more fully appreciated in view of the following detailed description of certain preferred embodiments.

A. Benzylpenicilloyl$_8$-Poly-L-Lysine$_8$ ($B_8L_8$)

1. Preparation

The PPL materials of my invention comprise a homogeneous polylysine carrier of from 6 to 12 degrees of polymerization in which at least about 66% of the coupling sites are occupied by conjugated penicilloyl groups derived from penicillins, cephalosporins or other β-lactam antibiotic moieties.

The novel $B_8L_8$ which is within the scope of my invention was prepared in the following manner:

Octa-L-lysine was prepared by the procedure of L. E. Barstow, et al. (Proc. Natl. Acad. Sci. U.S.A. 74:4248, 1977), with the following modifications. The starting material was α-t-BOC-E-CBZ-L-lysine Merryfield resin ester. There were seven consecutive couplings with α-t-BOC-E-CBZ-L-lysine with intermediate deprotection of the α-NH$_2$ group using trifluoroacetic acid (TFA). The resulting octa-L-lysine was deprotected and cleaved from the resin by mixing the resin at 25° C. for 25 minutes with TFA saturated with HBr gas (1 g resin per 10 ml TFA). HBr was removed by N$_2$ purge, and TFA was removed by evaporation under vacuum. The product was dissolved in H$_2$0 and lyophilized. The residue was then dissolved in 50% acetic acid and purified by chromatography through Sephadex G-15. The solution containing the major peak was diluted with H$_2$O to 10% acetic acid and lyophilized to yield a slightly yellow amorphous powder. The material was analyzed by paper chromatography using a modified Waley-Watson system (B. B. Levine and A. P. Redmond, J. Clinical Investigation 47:556, 1968). It showed one major spot corresponding to octa-L-lysine with traces at lysine$_6$ and lysine$_7$ (corresponding in color itensity to about 1% each).

100 mg of poly-L-lysine$_8$.HBr (assuming 90% peptide, 10% water) was dissolved in 25 ml deionized water and the pH was brought to 10±0.3 with 0.5M NaOH. A solution of 755 mg of potassium PG in 10 ml of water was added and the pH was brought to 11.5±0.05 with 0.5M NaOH. The reaction proceeded at room temperature (T=22° C.) with the reaction solution stirred by a magnetic stirrer and the pH maintained at 11.5±0.05 by additions of 0.5M NaOH. After two hours, when the reaction had gone to completion as evidenced by stability of the pH at 11.5, the solution was cooled to 5°–10° C. in an ice bath. The pH was brought down to pH 3.6 by additions of 1N HCl to the stirred solution. The white precipitate that formed was centrifuged down in a cold centrifuge. The precipitate was washed twice with small quantities of ice-cold deionized water. The precipitate was suspended in 20 ml of deionized water and dissolved by bringing the pH to 9.5–10.5 with 0.5M NaOH. The solution was clarified by cold centrifugation. The solution was cooled to 5°–10° C. and brought to pH 3.6 with 1N HCl. The white precipitate was centrifuged down and washed three times with small quantities of ice-cold deionized water. The moist precipitate was dried under very high vacuum in a lyophylizer. The yield was equal to 104 mg white powder about 55% of the theoretical.

In addition to the polylysine$_8$ derivative of PG described above, polylysine$_8$ derivatives can be prepared from all semi-synthetic penicillins. Thus, ampicillin, carbenicillin, napthacillin, oxacillin, cloxacillin, staphcillin, phenoxyethylpenicillin, phenoxymethylpenicillin, piparicillin, mezlocillin, etc. can be used to prepare corresponding PPL$_8$ derivatives. It is also expected to be possible to prepare useful polylysine$_8$ derivatives from cephalosporins and other $\beta$-lactam antibiotics. Methods other than precipitation at pH 3.7 can be used to isolate this or other final products, for example, preparative chromatographic methods or membrane separations may be used.

2. Preparation of Test Solution

A solution for use in skin testing for penicillin allergy or hypersensitivity using the above-described B$_8$L$_8$ was prepared as follows:

1.00 mg/ml was dissolved in 0.05M Na$_2$HPO$_4$. This was assayed by penamaldate assay which indicated the BPO concentration to be equal to $1.90 \times 10^{-3}$M. The total nitrogen content was assayed by the micro-Kjeldahl method and was determined to be 106 $\mu$g/ml. The nitrogen contribution from BPO was determined to be equal to $1.90 \times 28$ $\mu$g/ml or 53 $\mu$g/ml. The nitrogen contribution from polylysine$_8$ was determined to be equal to 106-53 or 53 $\mu$g/ml. The polylysine$_8$ equals $53 \times 4.65$ or 246 $\mu$g/ml which, when divided by 1042, equals $2.37 \times 10^{-4}$ M. The number of BPO groups per mol of polylysine$_8$ was calculated to be 8.02. Thus, the conjugate was determined to be B$_8$L$_8$, and the concentration of B$_8$L$_8$ in the stock solution of 1.00 mg/ml of B$_8$L$_8$ was determined to be $2.37 \times 10^{-4}$M.

3. Skin Tests Utilizing the B$_8$L$_8$ Solution

Skin testing using the novel B$_8$L$_8$ solution was conducted as follows:

The B$_8$L$_8$ stock solution was diluted to $1 \times 10^{-6}$ molar in tris-buffered saline with a pH of 8.2, also containing ethylenediaminetetraceticacid ($2 \times 10^{-4}$ molar) for stability. The composition was then used in skin testing. The tests were conducted by both the prick test and intradermal test methods, and the results were as follows:

Patient No. 1—prick test—B$_8$L$_8$=2+. The appearance of erythema and the size of the wheal (4-5 mm in diameter) indicated a positive reaction to the B$_8$L$_8$.

Patient No. 2—intradermal test—the B$_8$L$_8$ gave a 10 mm wheal and rated from 2+ to 3+ in intensity.

Other concentrations of th new PPL material can also be used for testing.

Additional non-allergic patients were tested in a similar fashion and showed negative reactions, indicating that the solutions were not primary irritants.

B. MDM Materials

Improved penicillin allergy or hypersensitivity skin testing can be achieved by use of an MDM which comprises an N-penicilloyl amine of an aliphatic amine, such as N-propyl amine or ethyl amine, or of an $\alpha$-aminoacid, such as $\alpha$-aminobutyric acid, norvaline, glutamine, proline, etc., as a new ingredient of the MDM, in addition to penicilloic acid and penicillin. These new materials (the N-penicilloyl amines of aliphatic amines or $\alpha$-aminoacids) detect IgE antibodies induced by penicillin which are undetected or only weakly detected by the currently utilized skin test materials. For example, Table II shows results of skin testing patients allergic to penicillin. Patients MB and CM gave more intense skin tests to BPO-ethyl amine and BPO-propyl amine than they did to the other minor determinant test materials. These BPO-alkyl amines do not reflect reactivity to either BPL or the other minor determinants, as there is no relationship between them. For example, patient CM was entirely negative to BPL while giving a positive reaction to BPO-ethyl amine and BPO-propyl amine. Note, also, positive reactions to BPO-propyl amine and BPO-ethyl amine associated with negative reactions to PG. Note that patients CM and MB gave stronger reactions to BPO-propyl amine and BPO-ethyl amine than to P/P (NaBPO plus POIC), while the reverse was true for patients LG and NT. Finally, note a lack of relationship between test intensities of BPO-amine and BPO-propyl amine.

The rationale for the use of a BPO-alkyl amine or aminoacid is that in some patients an important penicillin hapten or allergen may form from the reaction of penicillin with an amine or aminoacid present in blood plasma and tissue fluids. It has been hypothesized that NaBPO may become allergenic by first rearranging to benzylpenamaldic acid which can bind chemically to tissue proteins via mixed disulfide linkages to cysteine residues of protein.

Alternatively, benzylpenamaldic acid may degrade to benzylpenaldic acid (an aldehyde compound) which may react chemically with amino groups of protein binding via a Schiff base. The same sequence may be postulated for a penicilloyl-amine. Note that in both cases, the alkyl amine or aminoacid side chain would be an integral part of the haptenic group.

The alternatives which I have hypothesized are outlined in the following reactions:

C. Hypothetical Minor Haptenic Determinants

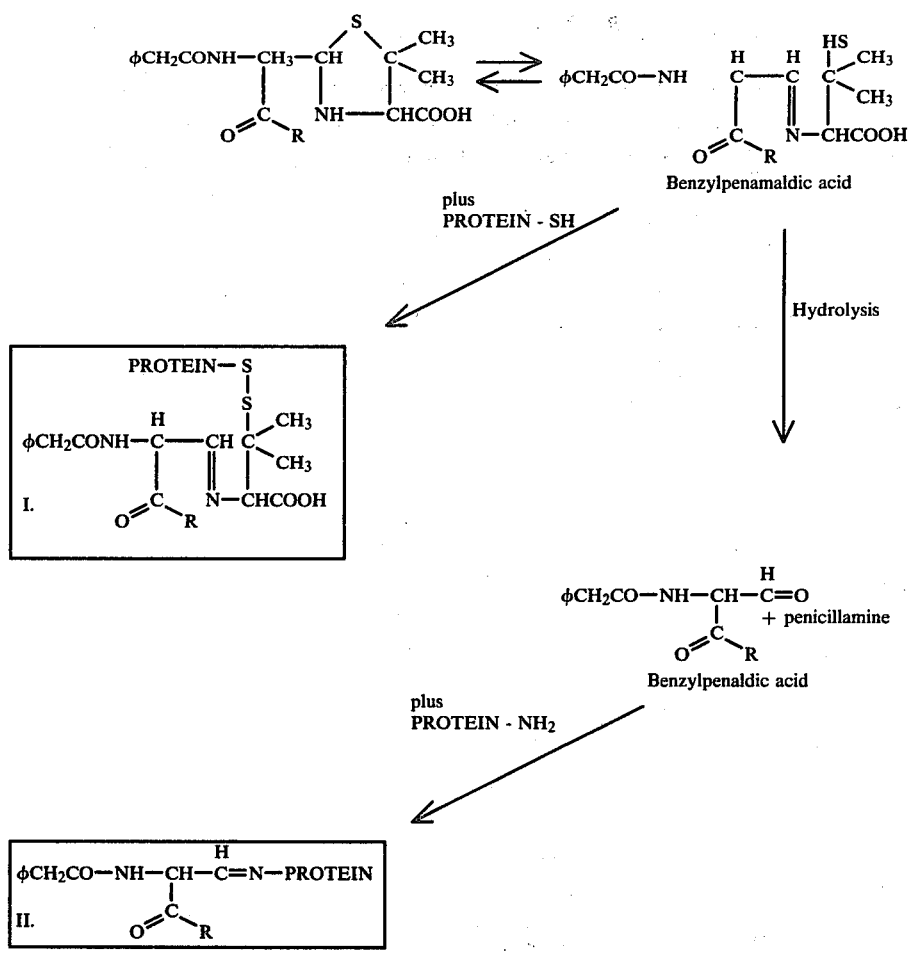

R=
Benzylpenicilloic acid —OH
Benzylpenicilloyl-propylamine —NHCH₂CH₂CH₃

In vivo, some of the circulating penicillin hydrolyses to penicilloic acid, and some may react with amines or aminoacids circulating in the plasma to form BPO-alkyl amines or BPO-aminoacids. Further rearrangement and/or degradation of the BPO-amines and reaction of those products with proteins as described above would result in the formation of allergenic hapten-protein conjugates. Some individuals may mount an immune response to one or more of these haptens. Skin testing with NaBPO, POIC or BPO-amine (which lack the alkyl amine or aminoacid side chain in their structures) may fail to detect IgE antibodies directed against the BPO-alkyl amine or BPO-aminoacid hapten in some patients. In some patients, some cross-reactivity between NaBPO and the BPO-alkyl amine (or aminoacid) probably exists, but a considerable decrease in ski test reaction intensity would result. Thus, testing with low concentrations of NaBPO (or testing by prick test, which amounts to the same thing) would fail to detect sensitivity, while testing with BPO-alkyl amine or BPO-aminoacid in low concentration or by prick test would be more likely to detect that sensitivity. In my new test, I intend to use the prick test to test patients without past histories of penicillin allergy who are about to be treated with penicillin or semi-synthetic penicillins or cephalosporins or other β-lactam antibiotics.

The preferred new MDM consists of NaBPO, PG and BPO-propyl amine (or BPO-ethyl amine or other BPO-alkyl amines or BPO-aminoacids in accordance with my invention). I believe that elimination of the BPO-amine and POIC from previously disclosed MDM mixtures would not cause lowered sensitivity, as a combination of NaBPO and BPO-propyl amine would detect those patients. BPO-propyl amine and BPO-ethyl amine were chosen as the preferred new MDM materials because their side chains are most similar to the majority of aminoacids and amines possible in view of the compounds found in blood and plasma. (See Tables IA, IB and IC for a listing of amines and aminoacids identified as being present in human blood and plasma.) Others may be added or substituted later. Following my invention, I believe that the aminoacid residue of my new MDM materials may be selected from any of the aminoacids found in blood plasma and tissue fluids, typical of which are those illustratively set forth in Tables IA., IB. and IC, as well as 2-aminopropanoic acid, 2-aminobutanoic acid, 2-aminopentanoic acid and 2-aminohexanoic acid. These latter four compounds are structurally similar to some amines and aminoacids found in blood. These N-penicilloyl amines and aminoacids may be α-diastereoisomers, other diastereoisomers or diastereoisomeric mixtures.

TABLE I

A. Aliphatic Amines In Blood Or Plasma[1]

| Amines | Concentration (mg/liter) | |
|---|---|---|
| | Mean | Range |
| Total aliphatic amines[2] (as Nitrogen) | 0.3 | (0.08–0.52) |
| Cystamine[2] $HSCH_2CH_2NH_2$ | 2.9 | |
| Spermine[2] $H_2N(CH_2)_3NH(CH_2)_4NH(CH_2)_3NH_2$ | 1.34 | (1.14–1.54) |
| Spermidine[2] $H_2N(CH_2)_3NH(CH_2)_4NH_2$ | 0.96 | (0.86–1.06) |
| Phosphoethanolamine[3] $HOPOCH_2CH_2NH_2$ with =O and OH on P | 0.5 | (0.0–1.1) |

[1] From "Scientific Tables", Diem & Lentner edit., 7th ed., 1970, Ciba-Geigy.
[2] Whole blood.
[3] Blood plasma.

TABLE I
B. Aminoacids In Blood Plasma[1]

| Aminoacid | Concentration (mg/liter) |
|---|---|
| Free aminoacid as α-$NH_2$ nitrogen | 42 |
| Alanine | 31 |
| Arginine | 14 |
| Cystine | 18 |
| Glutamine | 83 |
| Glycine | 17 |
| Histidine | 12 |
| Leucine | 13 |
| Lysine | 25 |
| Proline | 27 |
| Serine | 12 |
| Threonine | 19 |
| Valine | 20 |

[1] From CRC Handbook of Biochemistry.
The list presented here is incomplete.

TABLE I
C. Aminoacid Structures

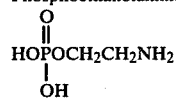

|  | where R = |
|---|---|
| Alanine | $-CH_3$ |
| Valine | $-CH(CH_3)_2$ |
| Leucine | $-CH_2CH(CH_3)_2$ |
| Asparagine | $-CH_2CONH_2$ |
| Glutamine | $-CH_2CH_2CONH_2$ |
| Lysine | $-(CH_2)_4NH_2$ |
| Histidine | (imidazole structure) |
| Proline | (Complete molecular structure) |

The invention, with respect to my novel MDM materials, compositions and skin testing methods, will be more fully appreciated by reference to the following detailed description.

D. Preparation Of BPO-amines, e.g., N-Dα-(benzylpenicilloyl)-amine

1. n-propyl amine derivative

26 g (0.07 mole) of potassium PG was dissolved in 200 ml of water. n-Propyl amine (6.2 g or 0.105 mole) was added dropwise to the stirred penicillin solution at room temperature (25° C.) under pH control. The pH was maintained at 11.2–11.5 for about 5 minutes, during which time about 0.07 moles of n-propyl amine was added. After that, the pH rose to 11.8–12.0 as the excess of n-propyl amine was added over an additional 5 minutes. The mixture was then stirred at room temperature for an additional 60 minutes.

The resulting solution was cooled to 5°–10° C. in an ice bath, and the pH adjusted to 3.8–4.0 by additions of 3N HCl to the stirred reaction mix. The resulting white precipitate was separated by filtration and washed extensively with cold water. The moist solid was dried under high vacuum.

y = 20 g white powder (70%).

Analysis: Calculated for $C_{19}H_{27}N_3O_4 S.H_2O$: C55.46 H7.10 N10.21 Found : C55.34 H6.79 N10.26

$[\alpha]^{26} = +111.2°$ (C, 1.006%, 0.2M phosphate buffer, pH 8.0)

2. n-ethyl amine derivative

37.3 g (0.10 mole) of potassium PG in 150 ml of water was treated with 6.9 g (0.15 mole) of ethyl amine in 20 ml of water added dropwise to the stirred penicillin solution over 10 minutes, as above for the propyl amine derivative. The reaction mixture was stirred for 45 minutes at room temperature, then lyophylized to give 41 g of crude material. The material was dissolved in 50 ml of 10% acetone-water, and the solution was cooled to 8° C. and adjusted to pH 3.9 with 3N HCl. The precipitate which formed was removed by filtration and washed 3 times with ice-cold water. The moist solid was dried under high vacuum.

y = 23 g white powder (60%).

Analysis: Calculated for $C_{18}H_{25}N_3O_4S.1.5H_2O$: C.53.19 H6.94 N10.34 Found : C.53.74 H6.53 N10.55

$[\alpha]^{26} = +125.0$ (C, 0.9712%, 0.2M phosphate buffer, pH 8.0)

3. n-butyl amine and n-amyl amine derivative

These were prepared in the same way using 1.5 g of the amine per equivalent of PG with precipitation of the product from the aqueous reaction mixture at 10° C. by adjusting the pH to 3.9±0.1.

E. Preparation of N-Dα-benzylpenicilloyl Aminoacid Derivatives

N-Dα-benzylpenicilloyl derivatives of α-aminoacids and other amines and aminoacids can be prepared. These include the natural aminoacids found in human blood plasma as shown in Table I as well as:

i. α-aminopropanoic acid (2-aminopropanoic acid)
ii. α-aminobutyric acid (2-aminobutanoic acid)
iii. α-aminovaleric acid (2-aminopentanoic acid)
iv. α-aminocaproic acid (2-aminohexanoic acid) (norleucine)

These aminoacids may be D, L or DL isomers.

Penicilloyl derivatives such as indicated above can be prepared from all semi-synthetic penicillins as well as from PG. Thus, ampicillin, amoxacillin, aczlocillin, carbenicillin, napthacillin, oxacillin, cloxacillin, mixtures, other diastereoisomers as well as the α-diastereoisomers. The above derivatives may also be prepared by other synthetic procedures, and the isolation and purification of the final products can also be done by other procedures.

The results of the penicillin allergy tests conducted by the procedures reported above are set forth in Table II,

TABLE II

Skin Test Reactions To BPO-amines And Other Penicillin Allergy Skin Test Materials Intensity of reactions in patients*

| Skin Test Material (Conc.) | LI | DL | NT | LG | RM | HD | CM | MB | HM |
|---|---|---|---|---|---|---|---|---|---|
| BPL $1 \times 10^{-6}$M | 1+ | 4+ | 0 | 1+ | 4+ | 4+ | 0 | 3+ | 0 |
| PG $1 \times 10^{-2}$M | 2+ | trace | 1+ | trace | 0 | 0 | 0 | 2+ | 0 |
| P/P $1 \times 10^{-}$M (of each ingredient) | 1+ | 1 − 2+ | 3+ | 2+ | 0 | 1+ | 1 − 2+ | 2+ | 2 − 3+ |
| BPO-amine $1 \times 10^{-2}$M | 1 − 2+ | trace | 2 − 3+ | 2+ | 0 | 1+ | 1+ | 1−2+ | 2 − 3+ |
| BPO-ethyl amine $1 \times 10^{-2}$M | 1 − 2+ | trace | 1 − 2+ | 0 | 0 | 1 − 2+ | 2+ | 3+ | 2 − 3+ |
| BPO-propyl amine $1 \times 10^{-2}$M | 1 − 2° | trace | 2+ | 1+ | 0 | 1 − 2+ | 2 − 3+ | 3 − 4+ | 2 − 3+ |
| Diluent control | 0 | 0 | 0 | 0 | 0 | 0 | 0 | 0 | 0 |

*Ten control patients gave negative skin tests to the skin test materials.

F. Skin Testing

The tests referred to above and in the following table were conducted as described below.

1. Skin test materials

Benzylpenicilloyl-polylysine (BPL) was a heterogeneous PPL preparation averaging benzylpenicilloyl$_7$-polylysine$_9$ (B$_7$L$_9$) at $1 \times 10^{-6}$M concentration of the conjugate in tris-buffered saline at pH 8.2.

Benzylpenicillin (PG) was $1.0 \times 10^{-2}$M in 0.11M saline.

Sodium benzylpenicilloate plus sodium benzylpenilloate (P/P) was $1.0 \times 10^{-2}$M of each dissolved in phosphate buffered saline at pH 7.5.

Benzylpenicilloyl-amine (BPO-amine) was $1.0 \times 10^{-2}$M concentration phosphate buffered saline at pH 7.5.

Benzylpenicilloyl-n-propyl amine and benzylpenicilloyl-n-ethyl amine (as α-diastereoisomers) were each dissolved to $1.0 \times 10^{-2}$M concentration in phosphate buffered saline at pH 7.5.

While aqueous solutions are described above, other suitable solvents may be used for both PPL and the MDM, e.g., 50/50 glycerol-water mixtures.

2. Patients

There were nine patients known to give positive skin test to penicillin derivatives. They were healthy men and women ranging in age from 23 to 56 years. Ten people negative to the skin test materials served as controls.

3. Skin test procedure

Using 1.0 ml tuberculin syringes with #26 needles and intradermal bevels, 0.01 ml volumes of the test materials were injected intradermally into the anterior-lateral aspects of the arms. Skin tests were read in 15 minutes. A negative reaction is the poorly outlined bleb of fluid —1–3 mm in diameter without surrounding erythema. Positive tests were sharply outlined wheals of 4–20 mm diameter with surrounding erythema. The positive tests were graded as 1+,2+,3+ and 4+ on the basis of wheal diameter. 1+ =4–6 mm; 2+ =7–9 mm; 3+ =10–12 mm; and 4+ =more than 13 mm with pseudopods. The stronger reactionshad wider circles of surrounding erythema which were more intensely red. Skin tests were done in duplicate. Duplicates gave identical or nearly identical readings.

4. Test results

What is claimed is:

1. A method for skin testing for allergy or hypersensitivity to penicillins, including benzyl penicillin and semi-synthetic penicillins, by the detection of minor determinant-specific skin sensitizing antibodies, such as, IgE antibodies or other skin sensitizing antibodies comprising prick, scratch or intradermal testing of the skin of a patient with solutions consisting essentially of (1) a compound represented by the formula:

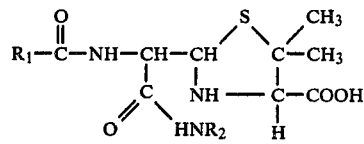

wherein:

R$_1$ is a side chain contained in the penicillins from which the penicilloyl amine or aminoacid compound is prepared; said penicillins being selected from the group consisting of benzylpenicillin and semi-synthetic penicillins, and R$_2$ is a substituent selected from the group consisting of an alkyl group of C$_2$–C$_6$ chain length, a carboxy alkyl group of C$_2$–C$_6$ chain length, or a residue of an aminoacid or amine compound of the type present in the blood, blood plasma or tissue fluids, said compound being selected from the group consisting of cystamine, spermine, spermidine, phosphoethanolamine, arginine, cystine, glutamine, histidine, lysine, proline, serine, threonine, and asparagine, said compounds being α-diastereoisomers, other diastereoisomers or diastereoisomeric mixtures; and (2) a suitable solvent for said compound (1), said solvent being compatible with the use of said composition in skin testing for penicillin allergy or hypersensitivity to penicillins, including benzyl penicillin and semisynthetic penicillins, the concentration of said compound (1) in said solvent (2) being sufficient to elicit a wheal and flare response in patients allergic or potentially allergic to said penicillins when said composition is administered to said patient in said skin testing but said concentration being optimal to avoid a constitutional reaction.

2. The method of claim 1 wherein said compound (1) is a compound wherein $R_1$ is a benzyl group and $R_2$ is an ethyl or N-propyl group.

3. The method of claim 1 wherein said compound (1) is an N-D-benzylpenicilloylaminopropane in any of its diastereoisomeric forms.

4. The method of claim 1 wherein said compound (1) is the N-D-benzylpenicilloylaminopropane, α-diastereoisomer.

5. The method of claim 1, 2, 3 or 4, wherein said solvent is an aqueous buffered saline solution.

* * * * *

UNITED STATES PATENT AND TRADEMARK OFFICE
CERTIFICATE OF CORRECTION

PATENT NO. : 4,183,910

DATED : January 15, 1980

INVENTOR(S) : Bernard B. Levine

It is certified that error appears in the above-identified patent and that said Letters Patent are hereby corrected as shown below:

IN THE ABSTRACT:

Second column, tenth line from bottom - after "penicillin" delete the comma (,) and insert -- --e.g., where $R_1 =$  ,--

IN THE SPECIFICATION:

In the formula at the top of Columns 7 and 8, right hand side, there should be a valence bond between "NH" and "C":

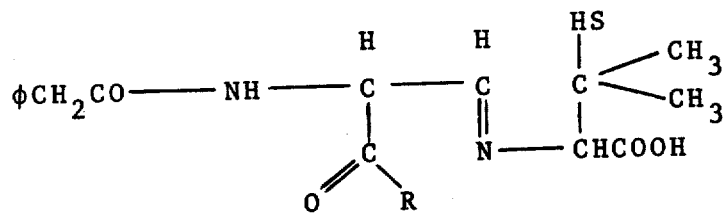

UNITED STATES PATENT OFFICE
CERTIFICATE OF CORRECTION

PATENT NO. : 4,183,910  
DATED : January 15, 1980  
INVENTOR(S) : Bernard B. Levine Page 2 of 2

It is certified that error appears in the above-identified patent and that said Letters Patent are hereby corrected as shown below:

Column 9, Table I, C, the first formula should read:

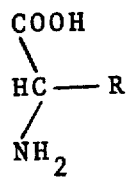

Column 10, line 65, after "cloxacillin," insert --staphcillin, phenoxyethylpenicillin, phenoxymethylpenicillin, piparicillin, mezlocillin, etc. can be used to prepare these penicilloyl derivatives. Possibly, cephalosporins and other β-lactam antibiotics may be used.

The N-penicilloyl amines and aminoacids derivatives such as indicated above can be prepared as diastereoisomeric--

Signed and Sealed this

Tenth Day of June 1980

[SEAL]

Attest:

SIDNEY A. DIAMOND

Attesting Officer

Commissioner of Patents and Trademarks